(12) United States Patent
Bice et al.

(10) Patent No.: US 12,344,624 B2
(45) Date of Patent: Jul. 1, 2025

(54) COMPLEX CONTAINING BETAINE, TRANSITION METAL AND SULFATE

(71) Applicant: BIOCHEM Zusatzstoffe Handels- und Produktionsgesellschaft mbH, Lohne (DE)

(72) Inventors: Ismet Bice, Rastede (DE); Heiko Greimann, Lohne (DE)

(73) Assignee: BIOCHEM Zusatzstoffe Handels- und Produktionsgesellschaft mbH, Lohne (DE)

( * ) Notice: Subject to any disclaimer, the term of this patent is extended or adjusted under 35 U.S.C. 154(b) by 305 days.

(21) Appl. No.: 17/928,292

(22) PCT Filed: Jun. 2, 2021

(86) PCT No.: PCT/EP2021/064824
§ 371 (c)(1),
(2) Date: Nov. 29, 2022

(87) PCT Pub. No.: WO2021/245148
PCT Pub. Date: Dec. 9, 2021

(65) Prior Publication Data
US 2023/0212206 A1 Jul. 6, 2023

(30) Foreign Application Priority Data
Jun. 4, 2020 (DE) .................... 10 2020 114 858.5

(51) Int. Cl.
*C07F 13/00* (2006.01)
(52) U.S. Cl.
CPC .......... *C07F 13/00* (2013.01); *C07B 2200/13* (2013.01)
(58) Field of Classification Search
None
See application file for complete search history.

(56) References Cited

U.S. PATENT DOCUMENTS 6,579,904 B1 * 6/2003 Hopps .................. A23K 20/105
556/50
12,103,901 B2 * 10/2024 Lamberts ............... A23K 20/30

OTHER PUBLICATIONS

Office action dated Jan. 11, 2021 in DE 102020114858 (2020) (German case in Family of U.S. Appl. No. 17/928,292) (downloaded Nov. 27, 2024) (Year: 2021).*
CAS Abstract and Indexed Compounds, US 2023/0212206 (2023) (Year: 2023).*
M. Fleck et al., Chapter 4 Compounds of Amino Acids and Neutral Salts in, Salts of Amino Acids, Crystallization, Structure and Properties, 139-206 (2014) (Year: 2014).*
J. Blachere et al. 3.4 X-Ray Diffraction Methods for the Characterization of Solid Pharmaceutical Materials, In Preformulation in Solid Dosage Form Development. CRC Press, 229-252 (2008) (Year: 2008).*
IUPAC, Compendium of Chemical Terminology, Gold Book, p. 344 of 1622, "coordination" (the "Gold Book") (2014) (Year: 2014).*
S. Patil et al., Exploration and investigation of periodic elements for electrocatalytic nitrogen reduction, 16 Small, 1-44 (2020) (Year: 2020).*
M Green, 500 Journal of Organometallic Chemistry, 127-148 (1995) (Year: 1995).*
T. Mak et al., 209 Zeitschrift fur Kristallographie, 354-356 (1994) (Year: 1994).*
X. Chen et al., 3 Structural Chemistry, 369-374 (1992) (Year: 1992).*
X. Chen et al., 189 Inorganica Chimica Acta, 3-5 (1991) (Year: 1991).*
CAS Abstract and Indexed Complex, X. Chen et al., 189 Inorganica Chimica Acta, 3-5 (1991) (Year: 1991).*
N. Greenwood et al., Chemistry of the Elements, Chapters 20-25, pp. 944-1112 (2nd ed., 1997) (Year: 1997).*
F. Tian et al., 62 Journal of Pharmacy and Pharmacology, 1534-1546 (2010) (Year: 2010).*
A.J. Cruz-Cabeza et al., 44 Chemical Society Reviews, 8619-8635 (2015) (Year: 2015).*
Anonymous: "Trimethylglycine", Wikipedia—retrieved Feb. 16, 2024; background information only as regards use of "betaine" as a common name for trimethylglycine.
Chen X.-M. et al.: A linear polymeric manganese(II) complex bridged by skew—skew bridging carboxylato groups. Crystal structure of catena-tris(betaine)maganese(II) tetrachloromanganate(II) (Mn(Me3NCH2COO)3)n nMnCl4; Inorganica Chimica Acta 1991, vol. 189, pp. 3-5.
Wiehl L. et al.: Crystal structures of catena-(tris(-betaine-O,O')manganese(II) tetrachlorozincate and catena(tris(µ-betaine-O,O')manganese(II) tetrachlorocobaltate, ((CH3)3NCH2COO)3Mn) (MCl4) (M=Zn, Co); Z. Kristallogr. NCS 221 (2006) 77-79.
Smith P. A. et al.: Ligand Mediated Morphology of the Two-Dimensional Uranyl Aqua Sulfates (UO2(×)(SO4)(H2O)) (X=Cl-or (CH3)3NCH2COO); Z. Anorg. Allg. Chem. 2019, 645, 504-508.
Mak T. C. W. et al.: Metal-betaine Interactions. XVIII. Crystal structure of tetraaqua-(trymethylammonioascetato) copper(III) sulfate trihydrate, (Cu(Me3NCH2CO2) (H2O)4) (SO4) 3 H2O; Zeitschrift für Kristallographie 209, 354-357.
Kulikov A. N., Deficit kompleksa mikroelementov v organizme životnyh i ih korrekciâ [Translation: Deficiency of the complex of microelements in the animal organism and its correction], thesis of a candidate of veterinary science course, Iževsk, 2018, 162 pp., pp. 6-10, in particular see p. 8; English translation attached to Russian article.
Galkina I. V. et al: Translation of Title: Synthesis and Structure of Metal Complexes Based on Zinc Chloride and Carboxylated Phosphabetaines; Scientific Notes of Kazan State University, vol. 152, Book 1 Natural Sciences 2010; English translation attached to Russian article.

* cited by examiner

*Primary Examiner* — Alexander R Pagano
(74) *Attorney, Agent, or Firm* — Gudrun E. Huckett

(57) ABSTRACT

Complex containing betaine, transition metal and sulfate in a ratio of 1:1:1, the transition metal being coordinated with two oxygen atoms from the betaine.

12 Claims, 10 Drawing Sheets

R= —CH$_2$—N(CH$_3$)$_3$
M= Zn

R= —CH$_2$—N(CH$_3$)$_3$
M= Mn

COMPLEX CONTAINING BETAINE, TRANSITION METAL AND SULFATE

BACKGROUND OF THE INVENTION

The invention relates to a complex containing betaine, transition metal and sulfate in a ratio of 1:1:1.

Certain transition metals are essential for humans and animals. Such transition metals can be provided to humans in the form of dietary supplements. For animals these transitions metals are added in optimum quantity to the feed itself. The presentation form of the transition metals on oral intake here is critical to the efficacy of the intake. Transition metals coordinated with organic compounds generally have a greater bioavailability for humans and animals than transition metals in inorganic compounds.

Betaine has been used for some considerable time already as a food and feed additive, in the form of betaine anhydrate or else betaine HCl. Betaine has positive effects for intestinal health and consequently on the absorption of nutrients. Another important property of betaine is its capacity to eliminate methyl groups, which are needed continuously for numerous metabolic processes, such as the construction of proteins in the human and in the animal. In cattle feed, the physiological demand for methyl groups is covered by native and added methionine, choline and betaine. Betaine is more efficient than choline in this respect, however. The reason for this greater efficiency is that choline must first be converted to betaine via two metabolic steps before it is able to deliver methyl groups. A disadvantage of betaine is a strong hygroscopy and the associated high sensitivity toward moisture, resulting in poor storability of the product.

U.S. Pat. No. 6,579,904 B1 describes the preparation of transition metal-betaine salts from starting materials comprising an alkali metal salt of chloroacetic acid, a water-soluble salt of a transition metal, and trimethylamine. As a consequence of its preparation, the salt contains a relatively large amount of chloride and also sodium. These impurities cannot be removed by customary ion exchangers, since such treatment could also entail removal of the transition metals as well which are desired in the end product. As raw materials, alkali metal acetate of chloroacetic acid and trimethylamine are toxic, moreover, and therefore necessitate costly and inconvenient storage and stringent safety measures during the preparation process.

By comparison with transition metal salts, betaine is more expensive. For an economically viable product, therefore, it is desirable to minimize the betaine fraction in the end product. In order to ensure the positive effect of the betaine on the bioavailability of the transition metals for the human or for the animal, however, there ought to be nevertheless at least one betaine molecule in the product per transition metal.

The invention is based on the object of providing an alternative complex containing betaine, transition metal and sulfate in a ratio of 1:1:1 that exhibits good stability.

SUMMARY OF THE INVENTION

The invention is achieved by a complex of the aforesaid type wherein the transition metal is coordinated with two oxygen atoms from betaine. These two oxygen atoms may belong to a single betaine molecule or else to two different betaine molecules within the complex. Coordinated in the sense of the invention means that there are the coordination bonds typical of complexes present between the transition metal and the two oxygen atoms from betaine. The transition metal is bonded organically in the complex and therefore exhibits high bioavailability. The complexes, moreover, have a high level of resistance to moisture and consequently have good storability.

The transition metal is preferably coordinated with two further oxygen atoms, but from sulfate. These two further oxygen atoms may come from a single sulfate molecule or else from two different sulfate molecules. With particular preference the two further oxygen atoms come from two different sulfate molecules when the two oxygen atoms from betaine with which the transition metal is coordinated can be assigned to a single betaine molecule. If, conversely, the transition metal is coordinated with two oxygen atoms from two different betaines, then with particular preference the transition metal is coordinated with two further oxygen atoms which come from a single sulfate molecule.

The complex of the invention is advantageously a polymer. The polymer chain here in a first preferred variant embodiment is formed by alternating molecules of metal and of sulfate (transition metal and sulfate in alternation), the transition metal being additionally coordinated with betaine. Betaine here is not a chain link but rather a chain appendage. In an advantageous configuration which is an alternative to this, the chain is formed by transition metal and betaine which alternate with one another, meaning that the chain is formed by metal molecules and betaine molecules which are coordinated with one another and which alternate with one another, the transition metal being additionally coordinated with sulfate. The sulfate here is not a chain member but rather a chain appendage. In the alternative configuration the sulfate, with particular preference, is coordinated exclusively with the transition metal.

In one particularly preferred configuration of the invention, the complex is a chelate complex with the transition metal as central atom. The chelate structure gives the complex a particularly stable design.

The complex advantageously has a heterocyclic ring structure with exactly four atoms, in which a transition metal atom is coordinated with two oxygen atoms and the two oxygen atoms are in turn each joined to the fourth atom within the ring. The fourth atom here, in a first advantageous variant of the invention, is formed by the carbon atom of the carboxylate group of the betaine. In this case, betaine with particular preference is the only chelator within the chelate structure. The transition metal is in this case additionally coordinated with sulfate molecules, but outside the chelate ring structure. In a further advantageous variant, the fourth atom is formed by the sulfur atom of the sulfate molecule. In this case the sulfate is preferably the only chelator within the chelate ring. The transition metal is in this case coordinated with betaine as further ligand, but outside the chelate ring.

In one particularly preferred configuration of the invention, the transition metal in the complex is formed by zinc, copper, iron or manganese.

The complex is advantageously an anhydrate. In an alternative configuration to this, the complex is preferably a dihydrate.

In one advantageous configuration of the invention, the transition metal is formed by zinc and the complex is characterized by an x-ray diffractogram which for Cu—$K_{\alpha 1}$ radiation at room temperature has powder x-ray diffraction peaks at 9.8, 11.7, 19.3, 21.1, 21.5, 22.4, 24.4 and 24.7 in degrees 2-theta, where each peak may have a standard deviation of up to +/−0.2 degrees 2-theta. With particular preference this complex is characterized by an x-ray diffractogram which for Cu—$K_{\alpha 1}$ radiation at room temperature has additional powder x-ray diffraction peaks at 17.7, 19.6, 29.8, 30.5, 31.8, 34.1, 34.3 and 34.5 in degrees 2-theta, and here as well each value has a standard deviation of up to +/−0.2 degrees 2-theta. With particular preference the aforesaid standard deviations are each only up to +/−0.1 degrees 2-theta. The compound advantageously is catena [µ3-sulfato(trimethylammonio)acetatozinc(II)].

In one advantageous configuration of the invention that is an alternative to this, the transition metal is formed by copper and the complex is characterized by an x-ray diffractogram which for Cu—$K_{\alpha 1}$ radiation at room temperature has powder x-ray diffraction peaks at 8.6, 10.3, 12.9, 16.7, 20.4, 20.7, 22.3 and 23.3 in degrees 2-theta, where each peak may have a standard deviation of up to +/−0.2 degrees 2-theta. With particular preference this complex is characterized by an x-ray diffractogram which for Cu—$K_{\alpha 1}$ radiation at room temperature has additional powder x-ray diffraction peaks at 11.1, 17.3, 19.9, 24.1, 25.7, 27.3, 27.8 and 28.5 in degrees 2-theta; here as well, each peak has a standard deviation of up to +/−0.2 degrees 2-theta. The standard deviation of the peaks in the x-ray diffractogram is advantageously in each case only up to +/−0.1 degrees 2-theta. With particular preference the complex is catena [µ3-sulfato(trimethylammonio)acetatocopper (II)].

In a further advantageous configuration of the invention, the transition metal is formed by manganese and the complex is characterized by an x-ray diffractogram which for Cu—$K_{\alpha 1}$ radiation at room temperature has additional powder x-ray diffraction peaks at 10.9, 12.9, 19.6, 20.3, 23.6, 23.9, 30.4 and 32.5 in degrees 2-theta, each peak with a standard deviation of up to +/−0.2 degrees 2-theta. With particular preference this complex is characterized by an x-ray diffractogram which for Cu—$K_{\alpha 1}$ radiation at room temperature has additional powder x-ray diffraction peaks at 19.1, 21.8, 22.5, 26.4, 27.4, 28.2, 30.9 and 31.8 in degrees 2-theta, here as well each peak has a standard deviation of up to +/−0.2 degrees 2-theta. With particular preference the standard deviation of the aforesaid peaks is in each case only +/−0.1 degrees 2-theta. With particular preference the complex is catena[µ3-sulfato(trimethylammonio)acetatomanganese(II)].

In a further alternative preferred configuration of the invention, the transition metal is formed by iron and the complex is characterized by an x-ray diffractogram which for Cu—$K_{\alpha 1}$ radiation at room temperature has powder x-ray diffraction peaks at 9.7, 14.1, 18.2, 18.5, 20.5, 21.0, 24.5 and 26.9 in degrees 2-theta, each peak with a standard deviation of up to +/−0.2 degrees 2-theta. With particular preference the complex is characterized by an x-ray diffractogram which for Cu—$K_{\alpha 1}$ radiation at room temperature has additional powder x-ray diffraction peaks at 13.4, 16.9, 21.6, 22.4, 24.0, 24.3, 27.2 and 28.7 in degrees 2-theta, each peak with a standard deviation of +/−0.2 degrees 2-theta. Advantageously the standard deviation of the aforesaid peaks is only up to +/−0.1 degrees 2-theta. With particular preference the complex is catena[diaquasulfato-µ2-(trimethylammonio)acetatoiron(II)].

In a further advantageous alternative configuration of the invention, the transition metal is formed by copper and the complex is characterized by an x-ray diffractogram which for Cu—$K_{\alpha 1}$ radiation at room temperature has powder x-ray diffraction peaks at 10.8, 12.3, 14.8, 17.4, 19.6, 19.9, 21.2 and 25.2 in degrees 2-theta, each peak with a standard deviation of up to +/−0.2 degrees 2-theta. With particular preference the complex is characterized by an x-ray diffractogram which for Cu—$K_{\alpha 1}$ radiation at room temperature has additional powder x-ray diffraction peaks at 16.0, 17.8, 22.7, 26.0, 26.3, 26.6, 31.8 and 32.2 in degrees 2-theta, each peak with a standard deviation of +/−0.2 degrees 2-theta. Advantageously the standard deviation of the aforesaid peaks is only up to +/−0.1 degrees 2-theta. With particular preference the complex is catena[diaquasulfato-µ2-(trimethylammonio)acetatocopper(II)].

In a further preferred alternative configuration of the invention, the transition metal is formed by manganese and the complex is characterized by an x-ray diffractogram which for Cu—$K_{\alpha 1}$ radiation at room temperature has powder x-ray diffraction peaks at 9.7, 14.1, 18.2, 18.5, 20.5, 21.0, 24.5 and 26.9 in degrees 2-theta, each peak with a standard deviation of up to +/−0.2 degrees 2-theta. With particular preference the complex is characterized by an x-ray diffractogram which for Cu—$K_{\alpha 1}$ radiation at room temperature has additional powder x-ray diffraction peaks at 13.4, 16.9, 21.6, 22.4, 24.0, 24.3, 27.2 and 28.7 in degrees 2-theta, each with a standard deviation of up to +/−0.2 degrees 2-theta. The standard deviation of the aforesaid peaks is advantageously in each case only up to +/−0.1 degrees 2-theta.

In one particularly preferred configuration of the invention, the chloride content of the complex is not more than 0.2% by weight. Advantageously the sodium content of the complex is not more than 0.5% by weight.

The complex of the invention is used advantageously in the nutrition of humans and/or animals.

Elucidated below in more detail are exemplary embodiments of the invention, their preparation, and the determination of the aforementioned powder x-ray diffraction peaks.

The metal contents were analyzed generally by the DIN EN 15621 method, using atomic emission spectrometry within inductively coupled plasma, and the water contents were determined by the common method R(EC) 152/2009, III, A at 103° C. for 4 hours. The nitrogen was analyzed according to method R(EC) 152/2009, III, C.

The x-ray powder diffractograms were measured in each case at room temperature with a STADI P powder diffractometer from Stoe & Cie, Darmstadt, in Guinier geometry between films, as a flat specimen. The radiation source was a Cu anode (40 kV, 20 mA); a Johann germanium monochromator generated Cu-Kalpha1 radiation (1.54059 angstroms). The detector employed was an Imageplate IP-PSD from Stoe & Cie.

DESCRIPTION OF PREFERRED EMBODIMENTS

Example 1

902 g of copper sulfate pentahydrate ($CuSO_4 \times 5\ H_2O$) are placed with stirring into 1.2 kg of water. Then 424 g of betaine anhydrate (($CH_3$)$_3NCH_2COO$) are added with stirring and the suspension is heated at 70° C. for 60 minutes. A dark blue clear solution is formed. The product is dried by fluidized bed spray granulation with the following parameters (table 1):

TABLE 1

Drying parameters for the copper-betaine complex from example 1 in the DMR WFP Koni

| Supply air temperature: | 120-160° C. | Supply air quantity: | 100-140 m³/h |
|---|---|---|---|
| Exhaust air temperature: | 80-90° C. | Nozzle (type/position) | 2x nozzles bottom spray |
| Product temperature: | 90-100° C. | Spraying pressure: | 1.5/2.0 bar |
| Feed temperature: | 80-85° C. | Spraying rate/ pump setting: | 13.8-30.6 g/min/— |

Figure 1:
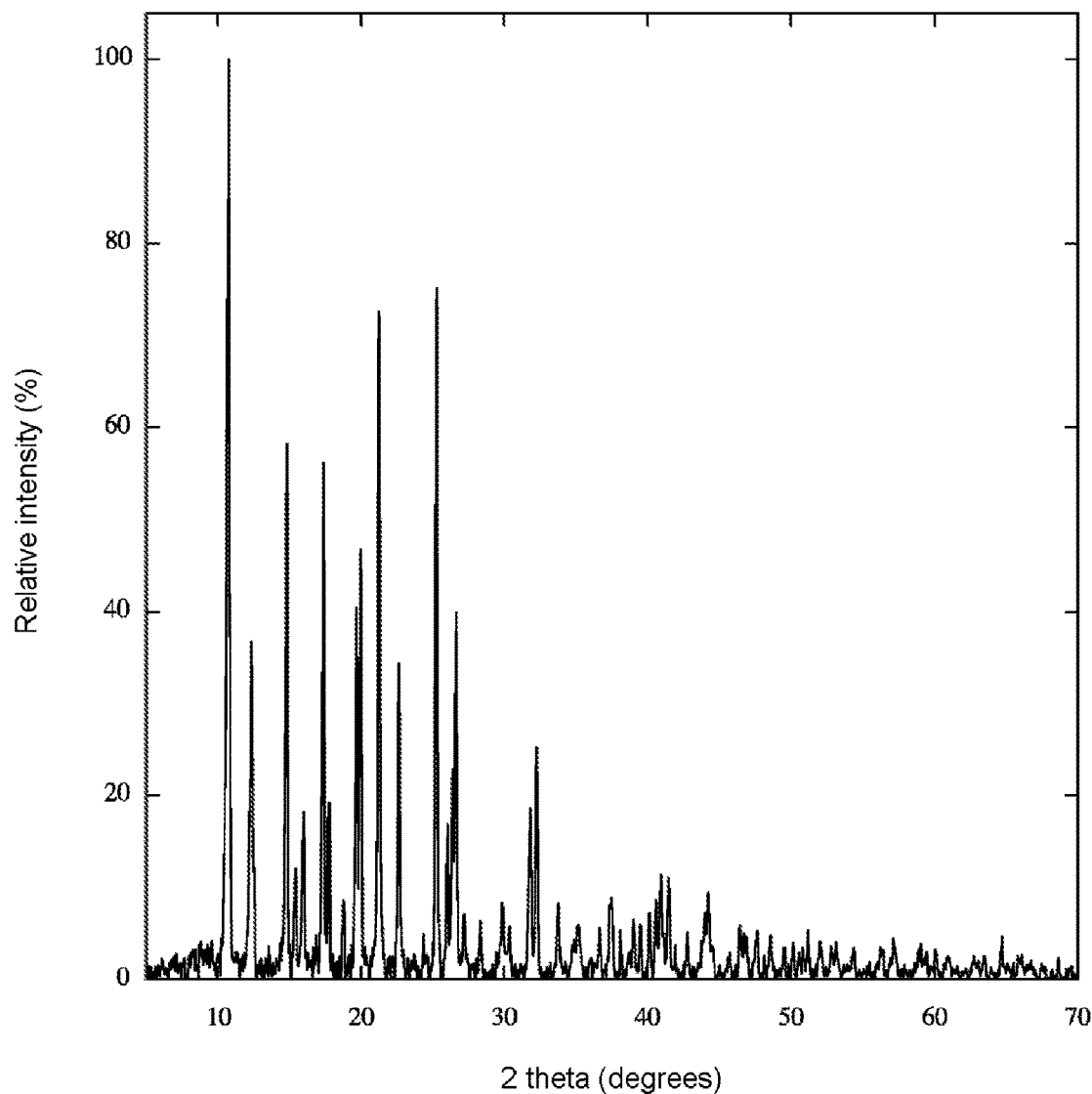
FIG. 1 shows the background-corrected x-ray diffractogram of the solid according to example 1 in the range 2°≤2 theta≤70°.

The green to turquoise, crystalline and granular product has a copper content of about 199 g/kg and a nitrogen content of about 44.2 g/kg. The background-corrected x-ray diffractogram of the solid according to example 1 is reproduced in FIG. 1 in the range 2°≤2 theta≤70°.

Table 2 lists the 2-theta- and d values and also the relative intensities of the reflections from the x-ray powder diffractogram of the solid according to example 1, where the measurement error of the 2 theta values may be +/−0.2 degree, preferably only +/−0.1 degree and more preferably only +/−0.05 degree, of the d values +/−0.02, and the measurement error of the relative intensities may be approximately +/−10 percentage points, preferably +/−5 percentage points.

TABLE 2

Representation of the 2-theta (degrees) and d values and relative intensities of the reflections from the x-ray powder diffractogram for example 1

| 2θ (degrees) | d (Å) | Relative intensity |
|---|---|---|
| 10.75 | 8.22 | 100 |
| 12.33 | 7.17 | 37 |
| 14.82 | 5.97 | 58 |
| 15.95 | 5.55 | 18 |
| 17.38 | 5.10 | 56 |
| 17.76 | 4.99 | 19 |
| 19.64 | 4.52 | 40 |
| 19.94 | 4.45 | 47 |
| 21.22 | 4.18 | 72 |
| 22.65 | 3.92 | 34 |
| 25.21 | 3.53 | 75 |
| 25.96 | 3.43 | 17 |
| 26.34 | 3.38 | 23 |
| 26.57 | 3.35 | 40 |
| 31.76 | 2.82 | 19 |
| 32.21 | 2.78 | 25 |

Example 2

902 g of copper sulfate pentahydrate ($CuSO_4 \times 5\ H_2O$) are placed with stirring into 1.2 kg of water. Then 424 g of betaine anhydrate (($CH_3$)$_3NCH_2COO$) are added with stirring and the suspension is heated at 90° C. for 120 minutes. A dark blue clear solution is formed. The product is dried by fluidized bed spray granulation with the following parameters (table 3):

TABLE 3

Drying parameters for the copper-betaine complex from example 2 in the DMR WFP Koni

| Supply air temperature: | 120-190° C. | Supply air quantity: | 90-150 m³/h |
|---|---|---|---|
| Exhaust air temperature: | 70-100° C. | Nozzle (type/position) | 2x nozzles bottom spray |
| Product temperature: | 71-110° C. | Spraying pressure: | 1.5/2.0 bar |
| Feed temperature: | 80-85° C. | Spraying rate/ pump setting: | 13.8-30.6 g/min/— |

Figure 2:
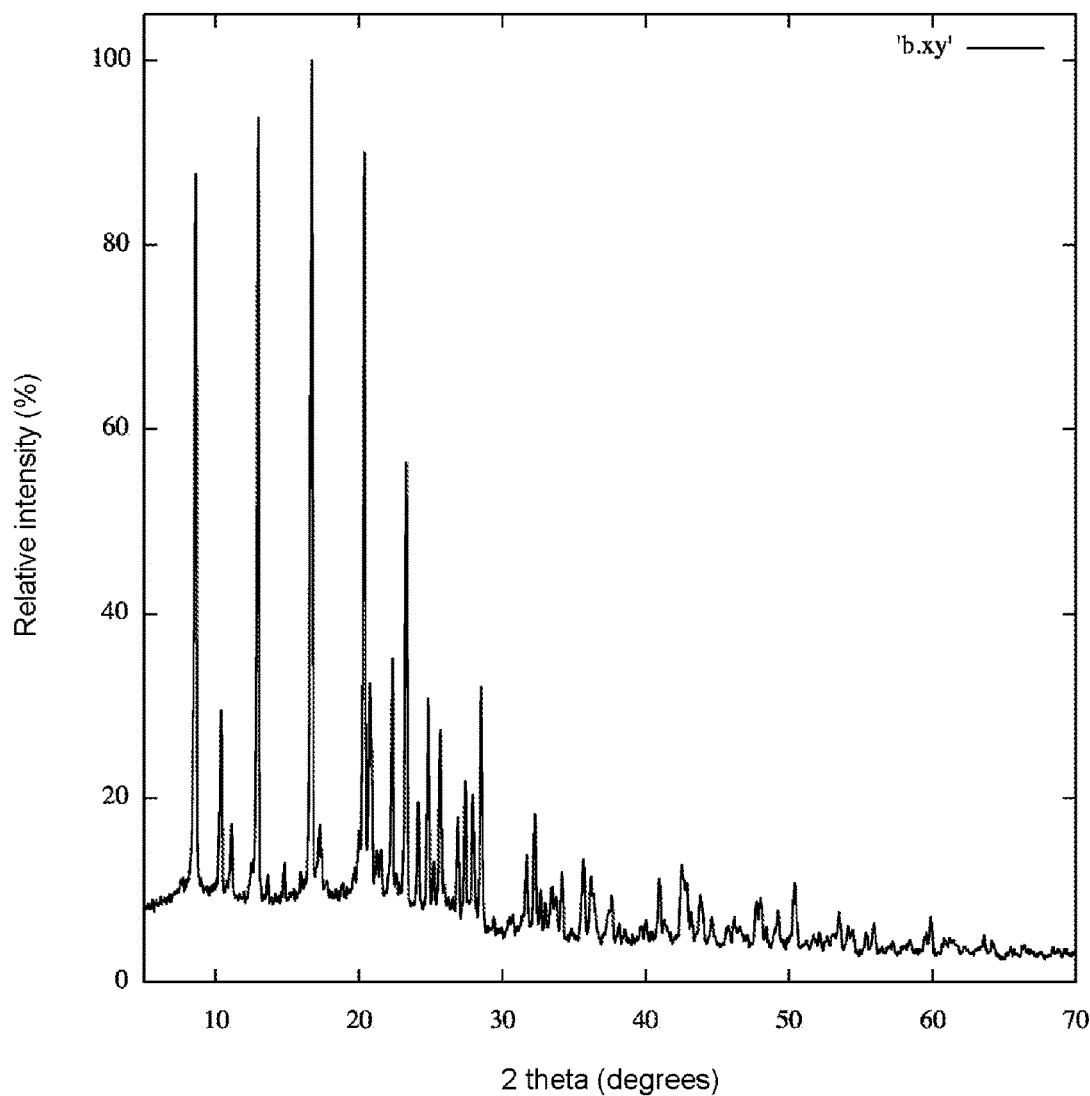
FIG. 2 shows the background-corrected x-ray powder diffractogram of the solid according to example 2 in the range 2°≤2 theta≤70°.

The green to turquoise, crystalline and granular product has a copper content of about 227 g/kg and a nitrogen content of about 50.1 g/kg. The background-corrected x-ray powder diffractogram of the solid according to example 2 is reproduced in FIG. 2 in the range 2°≤2 theta≤70°.

Table 4 lists the 2-theta values, d values and also the relative intensities of the reflections from the x-ray powder diffractogram of the solid according to example 2. The measurement error of the 2 theta values may be up to +/−0.2 degree, preferably up to +/−0.1 degree and more preferably up to +/−0.05 degree. The measurement error of the d values may be +/−0.02 and the measurement error of the relative intensities may be approximately +/−10 percentage points, preferably +/−5 percentage points.

TABLE 4

Representation of the 2-theta values (degrees) and d values and relative intensities of the reflections from the x-ray powder diffractogram for example 2

| 2θ (degrees) | d (Å) | Relative intensity |
|---|---|---|
| 8.64 | 10.22 | 88.0 |
| 10.30 | 8.58 | 30.0 |
| 11.12 | 7.94 | 17.6 |
| 12.93 | 6.83 | 93.8 |
| 16.70 | 5.30 | 100.0 |

TABLE 4-continued

Representation of the 2-theta values (degrees) and
d values and relative intensities of the reflections
from the x-ray powder diffractogram for example 2

| 2θ (degrees) | d (Å) | Relative intensity |
|---|---|---|
| 17.30 | 5.12 | 16.9 |
| 19.93 | 4.44 | 16.7 |
| 20.39 | 4.35 | 90.1 |
| 20.69 | 4.28 | 32.2 |
| 22.34 | 3.97 | 35.2 |
| 23.25 | 3.82 | 56.3 |
| 24.08 | 3.69 | 19.5 |
| 25.66 | 3.46 | 27.5 |
| 27.31 | 3.26 | 21.8 |
| 27.84 | 3.20 | 20.2 |
| 28.52 | 3.12 | 31.7 |

Example 3

644 g of zinc sulfate monohydrate ($ZnSO_4 \times 1\ H_2O$) are placed with stirring into 1.0 kg of water. Then 420 g of betaine anhydrate (($CH_3$)$_3NCH_2COO$) are added with stirring and the suspension is heated at 80° C. for 120 minutes. A clear solution is formed, which is dried by fluidized bed spray granulation to give a white granular powder. The drying parameters are set out in table 5.

TABLE 5

Drying parameters for the zinc-betaine chelate
from example 3 in the DMR WFP Koni

| Supply air temperature: | 170-200° C. | Supply air quantity: | 90-120 m³/h |
|---|---|---|---|
| Exhaust air temperature: | 70-90° C. | Nozzle (type/position) | 2x nozzles bottom spray |
| Product temperature: | 70-110° C. | Spraying pressure: | 1.5/2.0 |
| Feed temperature: | 80-85° C. | Spraying rate/ pump setting: | 10-50 g/min/ |

Determination of the single crystal structure:

A crystal in the form of a colorless block with approximate dimensions of 0.12×0.10×0.05 mm was selected and conveyed on a nylon loop into the $N_2$ cold gas stream of the diffractometer. During the measurement, a temperature of 100 K was maintained using an Oxford Cryostream 700. The intensity data were measured on a Bruker D8 goniometer with APEX CCD detector. The radiation source used for MoKα radiation (A=0.71073 Å) was an Incoatec I-μS microfocus tube with focusing multilayer optics.

6938 intensities were measured in w-scan mode and integrated with the aid of SAINT (Bruker 2009). For the scaling and absorption correction of the data on the basis of multiple determined reflections, the program SADABS (Bruker 2008) was employed.

The structure was resolved using direct methods (SHELXS, (Sheldrick 2008)) and refined to F2 with SHELXL-2018 (Sheldrick 2015). For the hydrogen atoms, isotropic deflection parameters were calculated on the basis of the anisotropically refined atoms bonded in each case. Hydrogen atoms bonded to C were calculated in standard geometry and included in the refinement. The refinement, for 2633 independent reflections and 130 variables, converged at quality factors of R=0.0217 (all reflections), R=0.0205 (observed reflections), wR2=0.0540, GOF=1.055. In a concluding differential Fourier synthesis, the remaining maxima and minima of the electron density proved to be +0.485 and −0.422 $eÅ^{-3}$ respectively.

Figure 3:
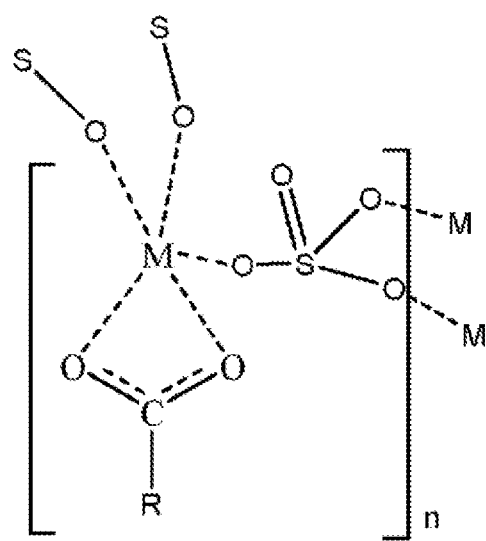
FIG. 3 shows the valence bond formula of the zinc-betaine chelate without charge.

The single crystal structural data are as follows: triclinic space group P-1, a=5.326, b=9.593, c=9.607 Å, α=102.6°, β=103.3°, γ=10.6° at T=100 K. The product obtained is catena[μ3-sulfato(trimethylammonio)acetatozinc(II)]. The chemical formula of the chelate is as follows: [Zn(($CH_3$)$_3NCH_2COO$)($SO_4$)]$_n$. The valence bond formula of the zinc-betaine chelate without charge is reproduced in FIG. 3.

Figure 4:
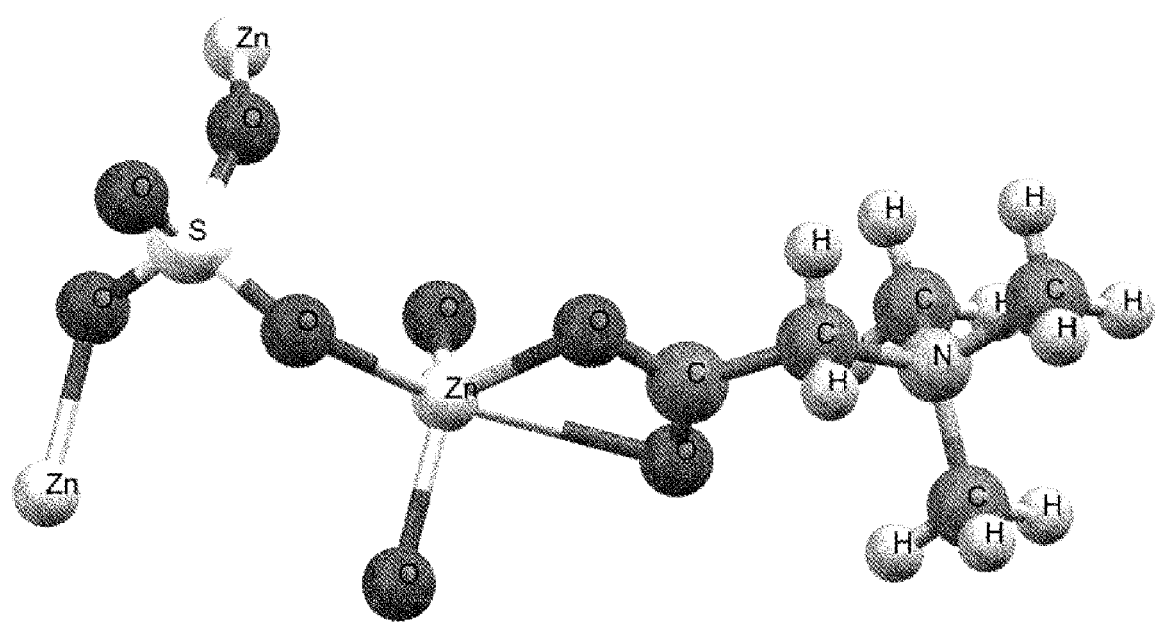
FIG. 4 shows the three-dimensional structure of the zinc-betaine chelate complex (single crystal structural analysis).
Figure 5:
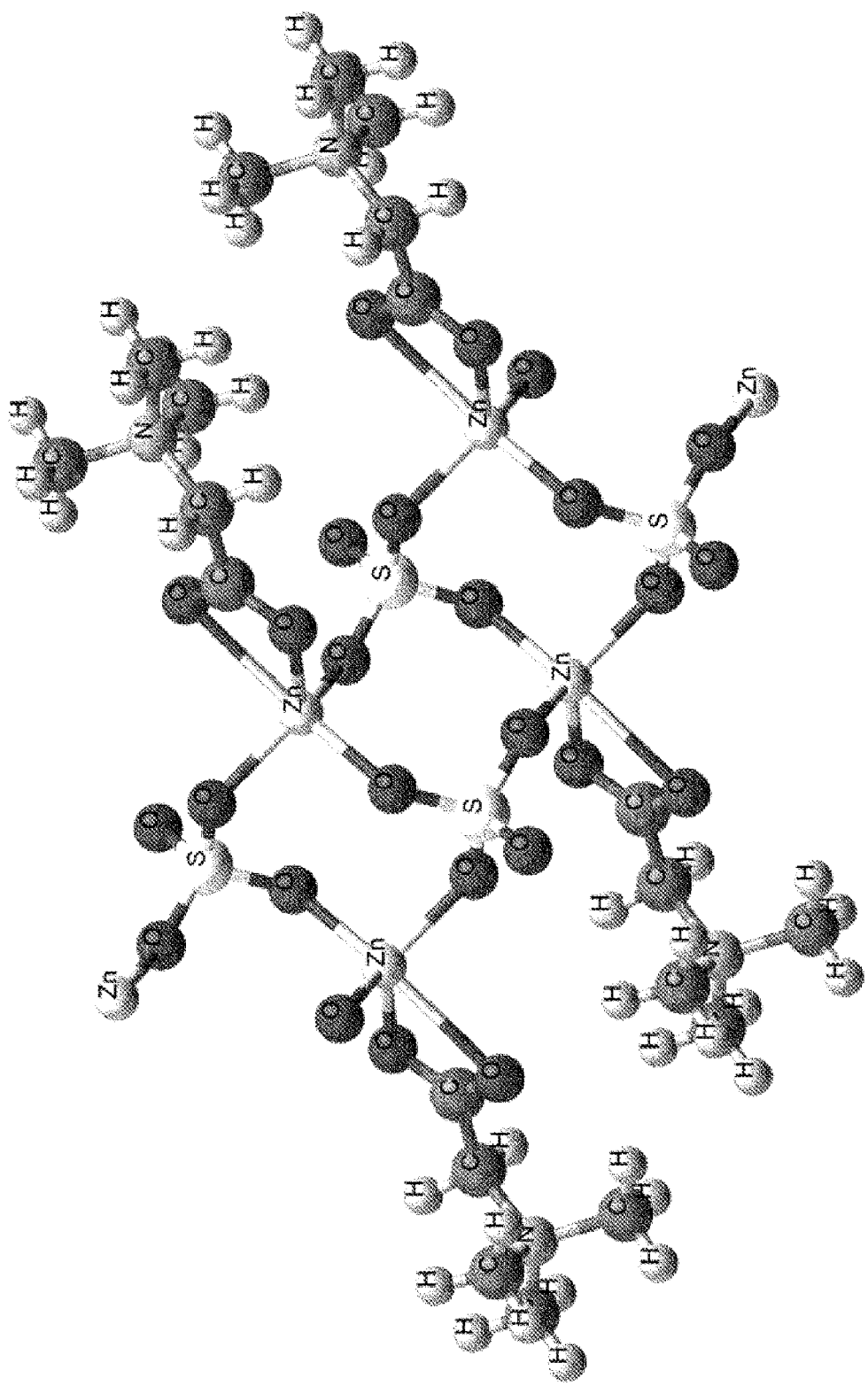
FIG. 5 shows the polymer structure for the zinc-betaine chelate complex.

The three-dimensional structure of this chelate is represented in FIG. 4 (structure for the zinc-betaine chelate complex (single crystal structural analysis)) and FIG. 5 (polymer structure for the zinc-betaine chelate complex). The white crystalline product has a zinc content of about 226 g/kg, a nitrogen content of about 49.1 g/kg and a surface water content of 18 g/kg.

Figure 6:
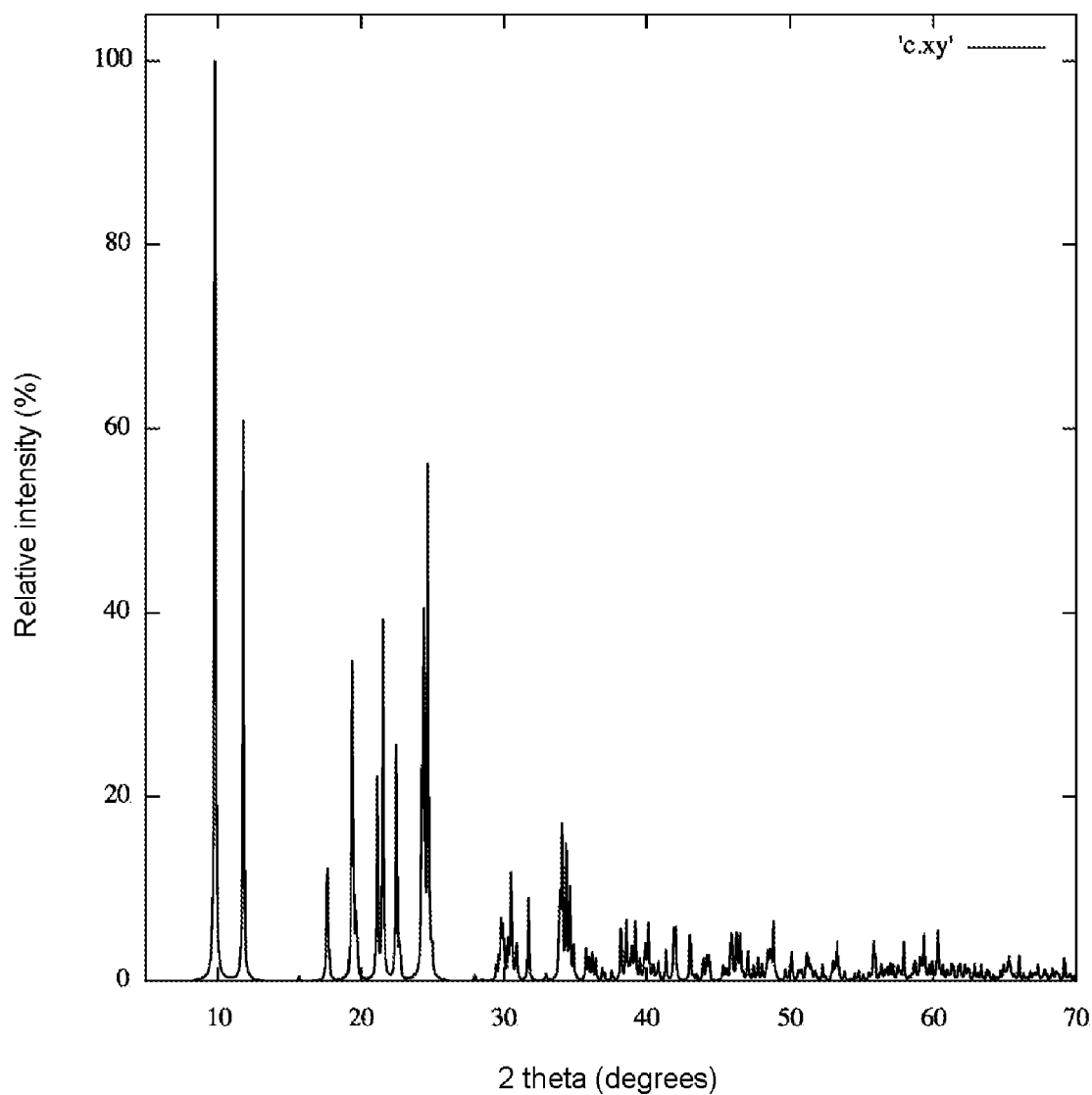
FIG. 6 shows the diffractogram (calculated on the basis of single crystal diffraction data) of the solid according to example 3 in the range 2°≤2 theta≤70°.

The diffractogram (calculated on the basis of single crystal diffraction data) of the solid according to example 3 is reproduced in FIG. 6 in the range 2°≤2 theta≤70°. Table 6 lists the 2-theta values, the d values and also the relative intensities of the reflections from the calculated x-ray powder diffractogram of the solid according to example 3. The measurement error of the 2 theta values specified is up to +/−0.2 degree, preferably up to +/−0.1 degree and more preferably up to only +/−0.05 degree. The measurement error of the d values is up to +/−0.02 and the measurement error of the relative intensities is up to +/−10 percentage points, preferably up to +/−5 percentage points.

TABLE 6

Representation of the 2-theta values (degrees) and d values
and relative intensities of the reflections from the
simulated x-ray powder diffractogram for example 3

| 2θ (degrees) | d (Å) | Relative intensity |
|---|---|---|
| 9.84 | 8.97 | 100.0 |
| 11.73 | 7.53 | 61.2 |
| 17.68 | 5.01 | 12.3 |
| 19.33 | 4.58 | 34.8 |
| 19.63 | 4.51 | 7.8 |
| 21.14 | 4.19 | 22.5 |
| 21.52 | 4.12 | 39.5 |
| 22.42 | 3.96 | 26.0 |
| 24.38 | 3.64 | 40.3 |
| 24.68 | 3.60 | 56.3 |
| 29.80 | 2.99 | 7.1 |
| 30.48 | 2.93 | 11.9 |
| 31.76 | 2.81 | 9.2 |
| 34.09 | 2.62 | 17.4 |
| 34.32 | 2.61 | 14.9 |
| 34.54 | 2.59 | 10.6 |

Example 4

556 g of manganese sulfate monohydrate ($MnSO_4 \times 1\ H_2O$) are placed with stirring into 1 kg of water. Then 385 g of betaine anhydrate (($CH_3$)$_3NCH_2COO$) are added with stirring and the suspension is heated at 70° C. for 60 minutes. A clear solution is formed, which is dried by fluidized bed spray granulation to give a pink-colored granular powder. The drying parameters are set out in table 7.

TABLE 7

Drying parameters for the manganese-betaine
complex from example 4 in the DMR WFP Koni

| Supply air temperature: | 140-170° C. | Supply air quantity: | 90-120 m³/h |
|---|---|---|---|
| Exhaust air temperature: | 80-90° C. | Nozzle (type/position) | 2x nozzles bottom spray |
| Product temperature: | 80-100° C. | Spraying pressure: | 1.5/2.0 |
| Feed temperature: | 80-85° C. | Spraying rate/ pump setting: | 10-20 g/min/ |

Determination of the Single Crystal Structure:

A crystal in the form of a colorless block with approximate dimensions of 0.09×0.07×0.04 mm was selected and conveyed on a nylon loop into the $N_2$ cold gas stream of the diffractometer. During the measurement, a temperature of 100 K was maintained using an Oxford Cryostream 700. The intensity data were measured on a Bruker D8 goniometer with APEX CCD detector. The radiation source used for MoKα radiation ($\lambda$=0.71073 Å) was an Incoatec I-μS microfocus tube with focusing multilayer optics.

16622 intensities were measured in w-scan mode and integrated with the aid of SAINT (Bruker 2009). For the scaling and absorption correction of the data on the basis of multiple determined reflections, the program SADABS (Bruker 2008) was employed.

The structure was resolved using direct methods (SHELXS, (Sheldrick 2008)) and refined to F2 with SHELXL-2018 (Sheldrick 2015). For the hydrogen atoms, isotropic deflection parameters were calculated on the basis of the anisotropically refined atoms bonded in each case. For the O—H distances of the water molecules, similar distances were ensured with a distance restraint. Hydrogen atoms bonded to C were calculated in standard geometry and included in the refinement. The refinement, for 3313 independent reflections and 160 variables, converged at quality factors of R=0.0568 (all reflections), R=0.0384 (observed reflections), wR2=0.1052, GOF=1.035. In a concluding differential Fourier synthesis, the remaining maxima and minima of the electron density proved to be +0.440 and −0.599 eÅ$^{-3}$ respectively.

Figure 7:
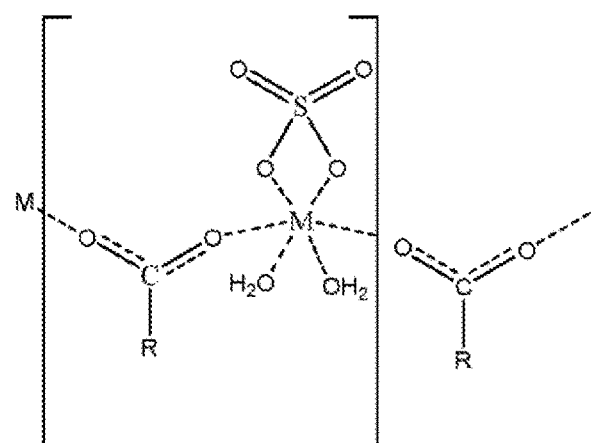
FIG. 7 shows the valence bond formula of the manganese-betaine complex without charge.
Figure 8:
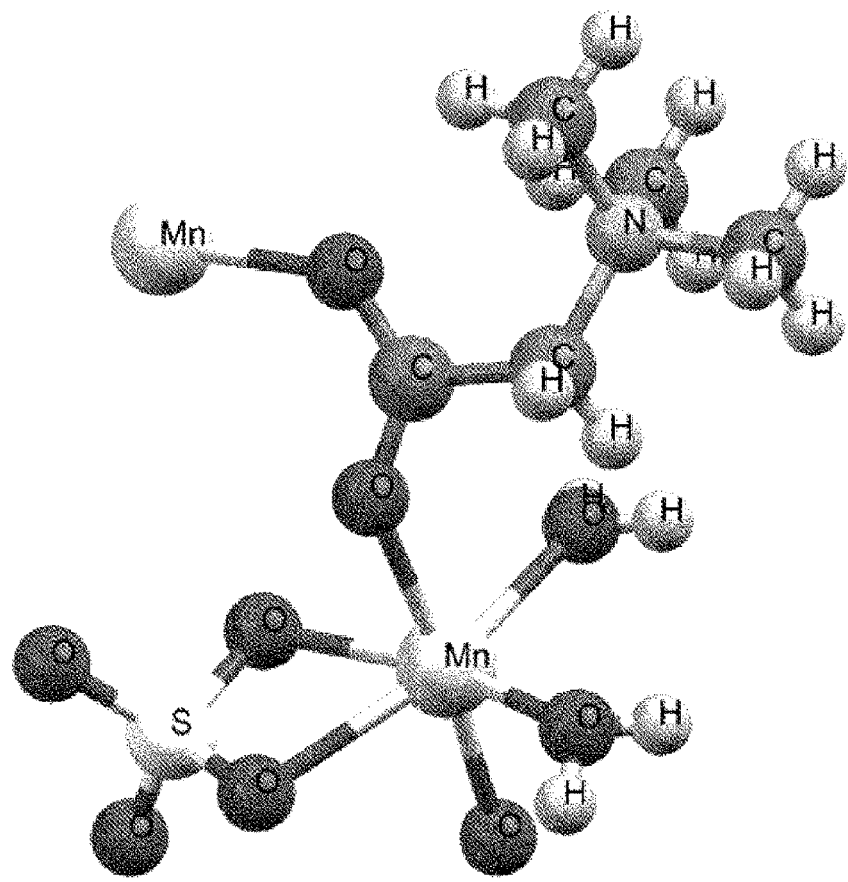
FIG. 8 shows the three-dimensional structure of the manganese-betaine complex (single crystal structural analysis).
Figure 9:
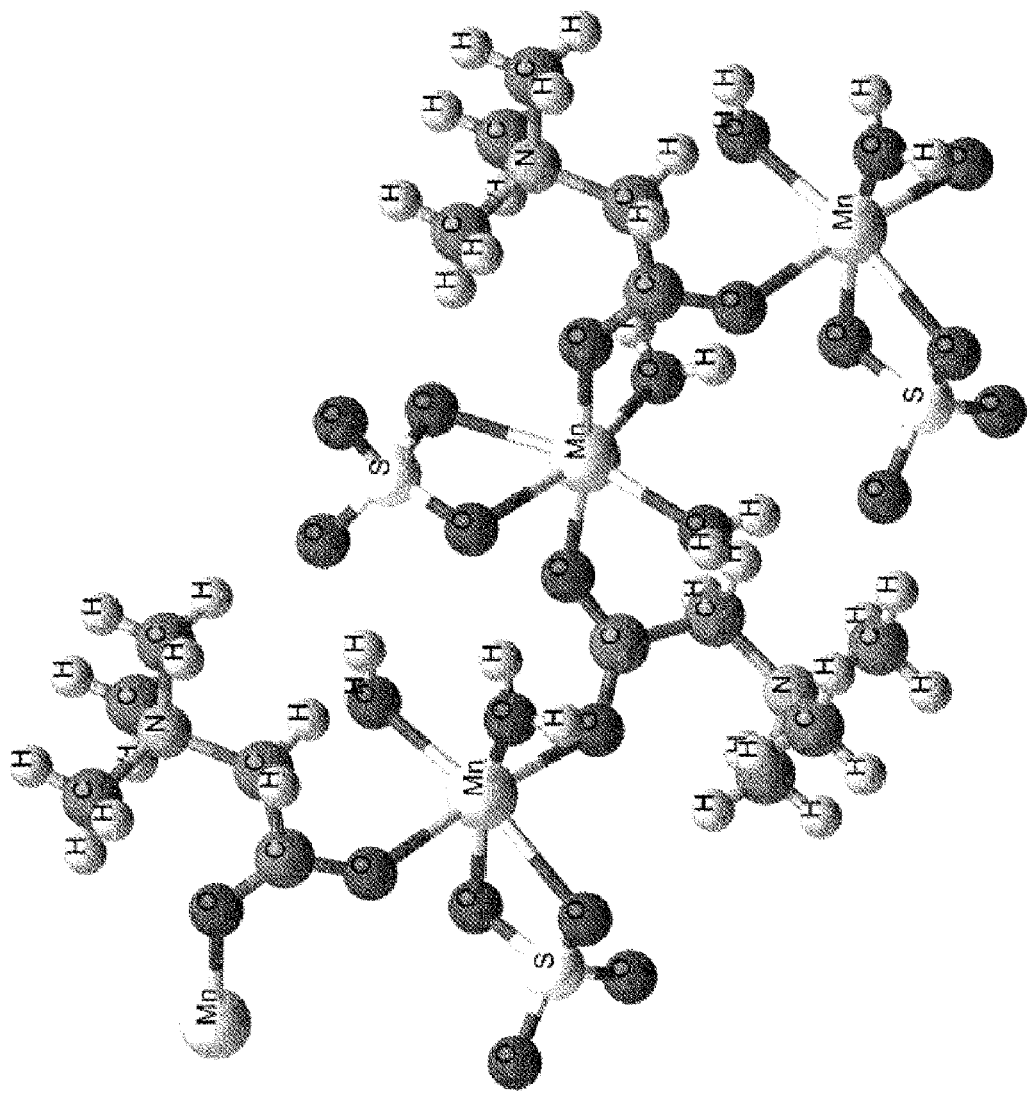
FIG. 9 shows the polymer structure of the manganese-betaine complex.

The single crystal structural data are as follows: monoclinic space group P21/c, a=9.184, b=9.586, c=12.681 Å, α=90°, β=97.7°, γ=90° at T=100 K. The product obtained is catena[diaqua-sulfato-μ2(trimethylammonio)acetatomanganese(II)]. The chemical formula of the chelate complex is as follows:

$[Mn(H_2O)_2((CH_3)_3NCH_2COO)(SO_4)]_n$. The valence bond formula of the manganese-betaine complex is reproduced without charge in FIG. 7. The three-dimensional structure of this complex is represented in FIG. 8 (structure of manganese-betaine complex (single crystal structural analysis)) and FIG. 9 (polymer structure of manganese-betaine complex).

The pink crystalline product had a manganese content of about 171 g/kg and a nitrogen content of about 46.1 g/kg.

Figure 10:
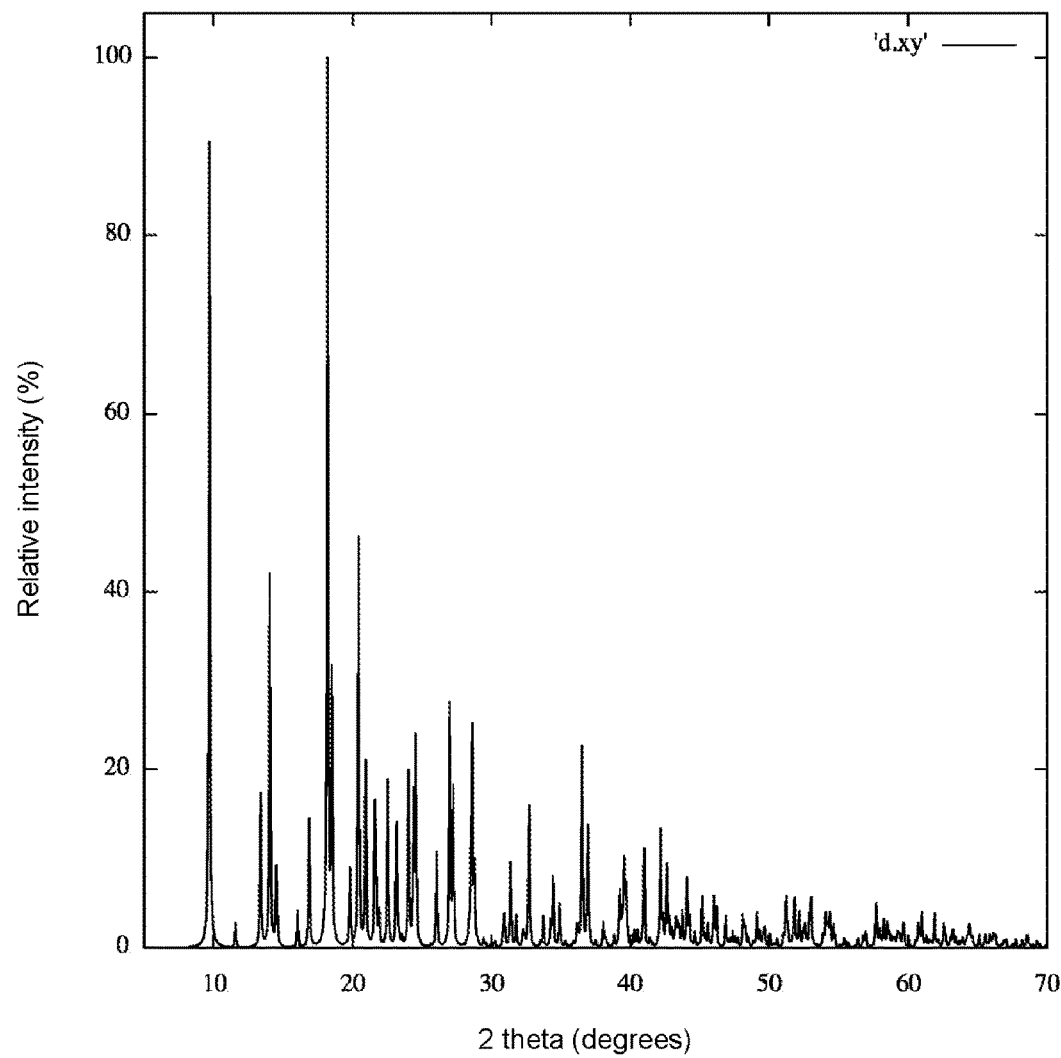
FIG. 10 shows the diffractogram (calculated on the basis of single crystal diffraction data) of the solid according to example 4 in the range 2°≤2 theta≤70°.

The diffractogram (calculated on the basis of single crystal diffraction data) of the solid according to example 4 is reproduced in FIG. 10 in the range 2°≤2 theta≤70°. Table 8 lists the 2-theta values, d values and relative intensities of the reflections from the x-ray powder diffractogram of the solid according to example 4. The measurement error of the 2 theta values specified is up to +/−0.2 degree, preferably up to +/−0.1 degree and more preferably up to only +/−0.05 degree. The measurement error of the d values is up to +/−0.02 and the measurement error of the relative intensities is up to +/−10 percentage points, preferably up to +/−5 percentage points.

TABLE 8

Representation of the 2-theta values (degrees) and d values
and relative intensities of the reflections from the
simulated x-ray powder diffractogram for example 4

| 2θ (degrees) | d (Å) | Relative intensity |
|---|---|---|
| 9.69 | 9.11 | 90.6 |
| 13.38 | 6.60 | 17.5 |
| 14.06 | 6.29 | 42.3 |
| 16.85 | 5.25 | 14.1 |
| 18.20 | 4.86 | 100.0 |
| 18.50 | 4.78 | 32.1 |
| 20.46 | 4.33 | 46.2 |
| 20.91 | 4.24 | 21.4 |
| 21.59 | 4.11 | 16.9 |
| 22.42 | 3.96 | 19.2 |
| 24.00 | 3.70 | 19.8 |
| 24.30 | 3.65 | 18.0 |
| 24.53 | 3.62 | 23.9 |
| 26.94 | 3.30 | 27.6 |
| 27.16 | 3.27 | 18.4 |
| 28.67 | 3.11 | 25.3 |

Example 5

556 g of manganese sulfate monohydrate ($MnSO_4$×1 $H_2O$) are placed with stirring into 1 kg of water. Then 385 g of betaine anhydrate (($CH_3$)$_3NCH_2COO$) are added with stirring and the suspension is heated at 90° C. for 120 minutes. A clear solution is formed, which is dried by fluidized bed spray granulation to give a pink-colored granular powder. The drying parameters are set out in table 9.

TABLE 9

Drying parameters for the manganese-betaine
complex from example 5 in the DMR WFP Koni

| Supply air temperature: | 180-200° C. | Supply air quantity: | 90-120 m³/h |
|---|---|---|---|
| Exhaust air temperature: | 85-95° C. | Nozzle (type/position) | 2x nozzles bottom spray |
| Product temperature: | 100-110° C. | Spraying pressure: | 1.5/2.0 |
| Feed temperature: | 80-85° C. | Spraying rate/ pump setting: | 10-20 g/min/ |

Figure 11:
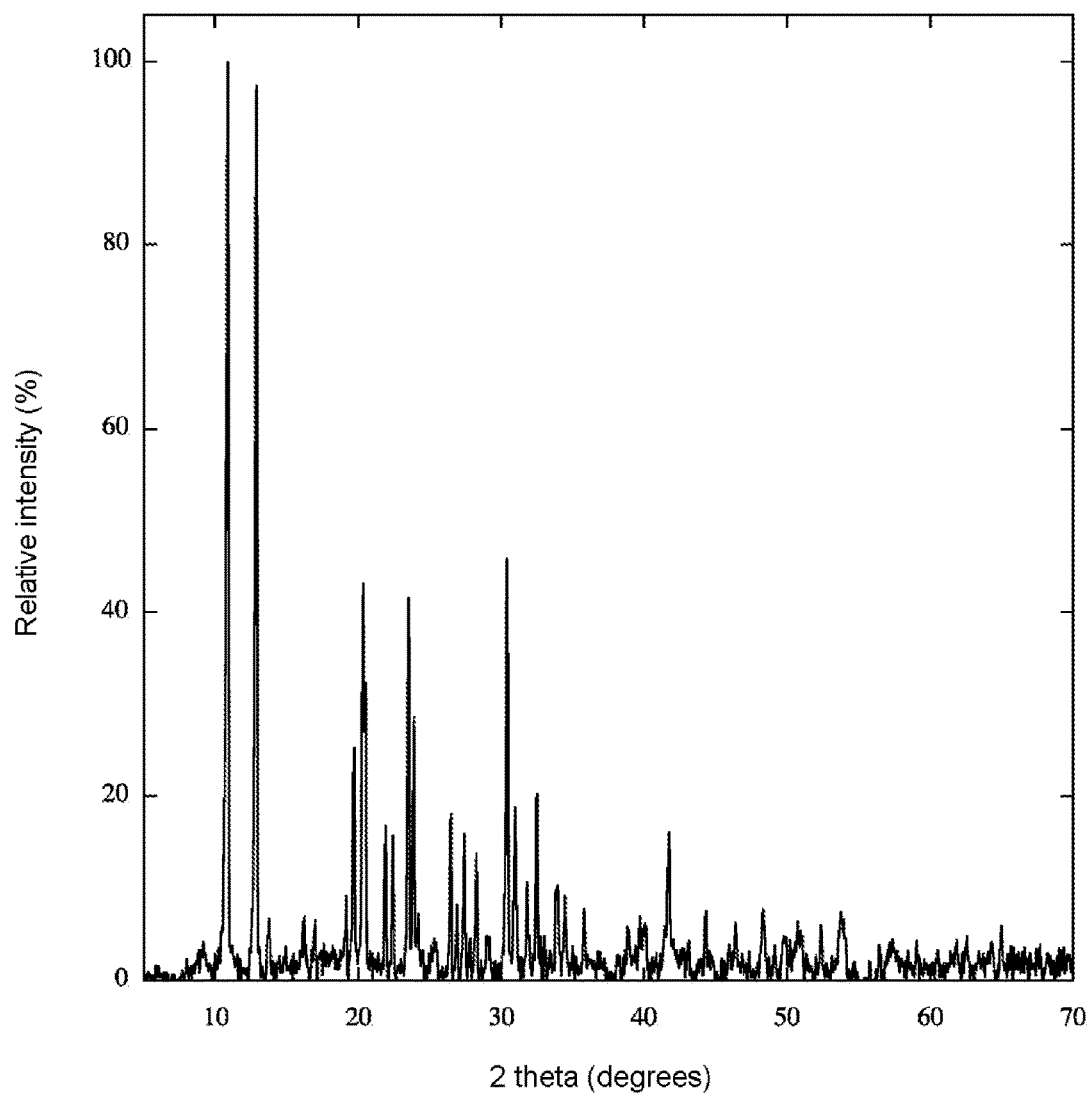
FIG. 11 shows the background-corrected x-ray powder diffractogram of the solid according to example 5 in the range 2°≤2 theta≤70°.

The pink crystalline product had a manganese content of about 191 g/kg, a nitrogen content of about 51.2 g/kg and a surface water content of 10 g/kg. The background-corrected x-ray powder diffractogram of the solid according to example 5 is reproduced in FIG. 11 in the range 2°≤2 theta ≤70°.

Table 10 lists the 2-theta values, d values and relative intensities of the reflections from the x-ray powder diffractogram of the solid according to example 5. The measurement error of the 2 theta values specified is up to +/−0.2 degree, preferably up to +/−0.1 degree and more preferably up to only +/−0.05 degree. The measurement error of the d values is up to +/−0.02 and the measurement error of the relative intensities is up to +/−10 percentage points, preferably up to +/−5 percentage points.

TABLE 10

Representation of the 2-theta values (degrees) and d values and relative intensities of the reflections from the x-ray powder diffractogram for example 5

| 2θ (degrees) | d (Å) | Relative intensity |
|---|---|---|
| 10.90 | 8.11 | 100 |
| 12.86 | 6.88 | 98 |
| 19.11 | 4.64 | 9 |
| 19.64 | 4.52 | 25 |
| 20.32 | 4.37 | 44 |
| 21.82 | 4.07 | 17 |
| 22.50 | 3.95 | 16 |
| 23.55 | 3.77 | 42 |
| 23.86 | 3.73 | 29 |
| 26.42 | 3.37 | 18 |
| 27.39 | 3.25 | 16 |
| 28.22 | 3.16 | 14 |
| 30.41 | 2.94 | 46 |
| 30.93 | 2.89 | 19 |
| 31.84 | 2.81 | 11 |
| 32.52 | 2.75 | 21 |

Example 6

557 g of iron sulfate monohydrate ($FeSO_4 \times 1\ H_2O$) are placed with stirring into 1.0 kg of water. Then 383.8 g of betaine anhydrate (($CH_3$)$_3NCH_2COO$) are added with stirring and the suspension is heated at 80° C. for 60 minutes. A clear solution is formed, which is dried by fluidized bed spray drying to give a brown granular powder. The drying parameters are set out in table 11.

TABLE 11

Drying parameters for the iron-betaine compound from example 6 in the DMR WFP Koni

| Supply air temperature: | 120-160° C. | Supply air quantity: | 90-120 m³/h |
|---|---|---|---|
| Exhaust air temperature: | 80-90° C. | Nozzle (type/position) | 2x nozzles bottom spray |
| Product temperature: | 70-100° C. | Spraying pressure: | 1.5/2.0 |
| Feed temperature: | 80-85° C. | Spraying rate/ pump setting: | 6-19 g/min/ |

The brown crystalline product has an iron content of about 151 g/kg, a nitrogen content of about 4.54 g/kg and a surface water content of 21 g/kg. The structure is isomorphic to example 4.

Figure 12:
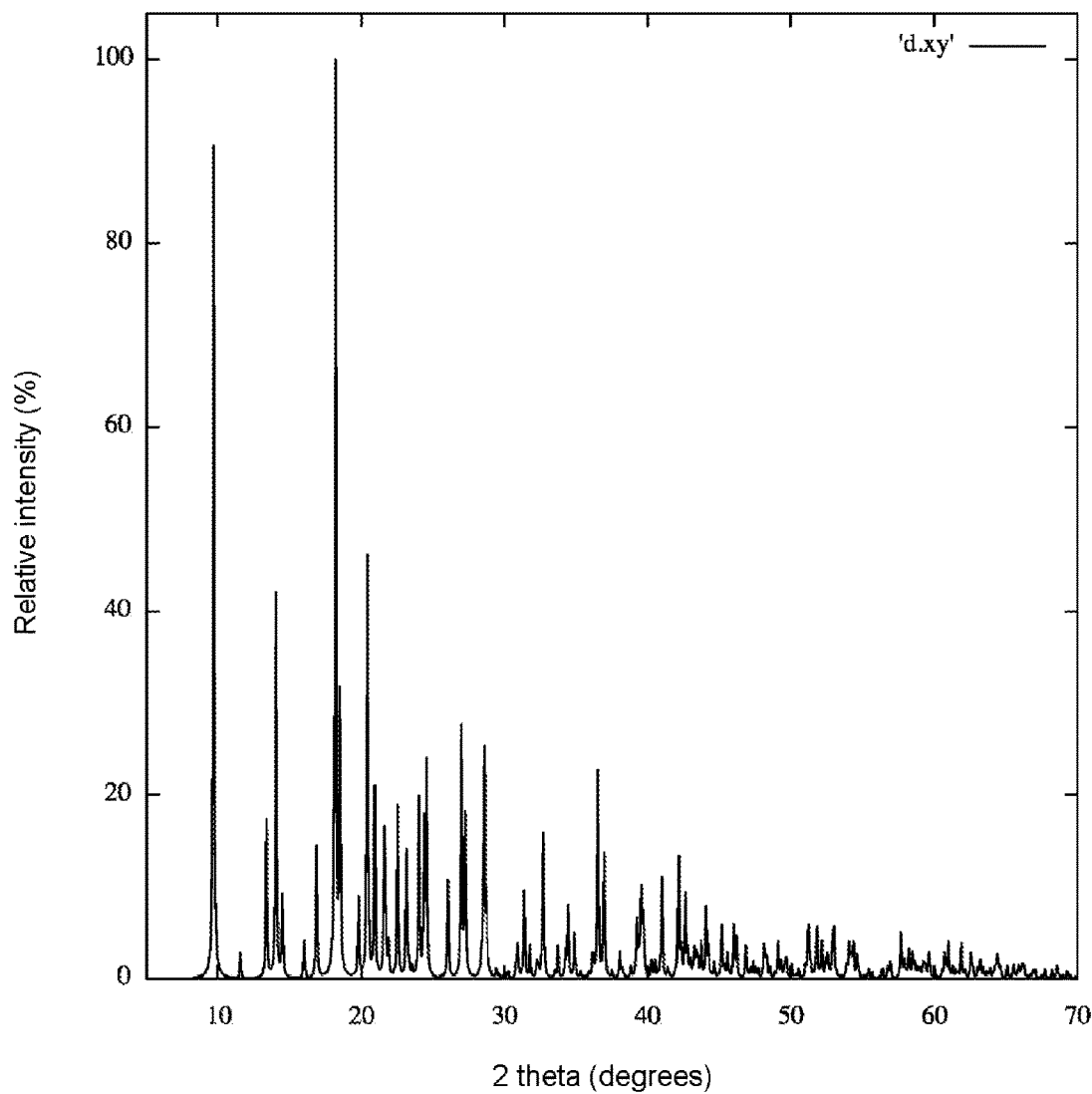
FIG. 12 shows the diffractogram (calculated on the basis of single crystal diffraction data) of the solid according to example 6 in the range 2°≤2 theta≤70°.

The diffractogram (calculated on the basis of single crystal diffraction data) of the solid according to example 6 is reproduced in FIG. 12 in the range of 2°≤2 theta≤70°. Table 12 lists the 2-theta values, d values and relative intensities of the reflections from the x-ray powder diffractogram of the solid according to example 6. The measurement error of the 2-theta values specified is up to +/−0.2 degree, preferably up to +/−0.1 degree and more preferably up to only +/−0.05 degree. The measurement error of the d values is up to +/−0.02 and the measurement error of the relative intensities is up to +/−10 percentage points, preferably up to +/−5 percentage points.

TABLE 12

Representation of the 2-theta values (degrees) and d values and relative intensities of the reflections from the simulated x-ray powder diffractogram for example 6

| 2θ (degrees) | d (Å) | Relative intensity |
|---|---|---|
| 9.69 | 9.11 | 90.6 |
| 13.38 | 6.60 | 17.5 |
| 14.06 | 6.29 | 42.3 |
| 16.85 | 5.25 | 14.1 |
| 18.20 | 4.86 | 100.0 |
| 18.50 | 4.78 | 32.1 |
| 20.46 | 4.33 | 46.2 |
| 20.91 | 4.24 | 21.4 |
| 21.59 | 4.11 | 16.9 |
| 22.42 | 3.96 | 19.2 |
| 24.00 | 3.70 | 19.8 |
| 24.30 | 3.65 | 18.0 |
| 24.53 | 3.62 | 23.9 |
| 26.94 | 3.30 | 27.6 |
| 27.16 | 3.27 | 18.4 |
| 28.67 | 3.11 | 25.3 |

What is claimed is:

1. A complex containing one or more betaine molecules, one or more transition metals, and one or more sulfate molecules in a ratio of 1:1:1, wherein the one or more transition metals each are coordinated with two oxygen atoms of a single one of the betaine molecules or with two oxygen atoms of two different ones of the one or more betaine molecules, wherein the transition metal is zinc and the complex is characterized by an x-ray diffractogram having, for Cu-Kα1 radiation at room temperature, powder x-ray diffraction peaks at 9.8, 11.7, 19.3, 21.1, 21.5, 22.4, 24.4, and 24.7 in degrees 2-theta, each with a standard deviation of +/−0.2 degrees 2-theta.

2. A complex containing one or more betaine molecules, one or more transition metals, and one or more sulfate molecules in a ratio of 1:1:1, wherein the one or more transition metals each are coordinated with two oxygen atoms of a single one of the betaine molecules or with two oxygen atoms of two different ones of the one or more betaine molecules, wherein the transition metal is copper and the complex is characterized by an x-ray diffractogram having, for Cu-Kα1 radiation at room temperature, powder x-ray diffraction peaks at 8.6, 10.3, 12.9, 16.7, 20.4, 20.7, 22.3, and 23.3 in degrees 2-theta, each with a standard deviation of +/−0.2 degrees 2-theta.

3. A complex containing one or more betaine molecules, one or more transition metals, and one or more sulfate molecules in a ratio of 1:1:1, wherein the one or more transition metals each are coordinated with two oxygen atoms of a single one of the betaine molecules or with two oxygen atoms of two different ones of the one or more betaine molecules, wherein the transition metal is manganese and the complex is characterized by an x-ray diffractogram having, for Cu-Kα1 radiation at room temperature, powder x-ray diffraction peaks at 10.9, 12.9, 19.6, 20.3, 23.6, 23.9, 30.4, and 32.5 in degrees 2-theta, each with a standard deviation of +/−0.2 degrees 2-theta.

4. A complex containing one or more betaine molecules, one or more transition metals, and one or more sulfate molecules in a ratio of 1:1:1, wherein the one or more transition metals each are coordinated with two oxygen atoms of a single one of the betaine molecules or with two oxygen atoms of two different ones of the one or more betaine molecules, wherein the transition metal is iron and the complex is characterized by an x-ray diffractogram having, for Cu-Kα1 radiation at room temperature, powder x-ray diffraction peaks at 9.7, 14.1, 18.2, 18.5, 20.5, 21.0, 24.5, and 26.9 in degrees 2-theta, each with a standard deviation of +/−0.2 degrees 2-theta.

5. A complex containing one or more betaine molecules, one or more transition metals, and one or more sulfate molecules in a ratio of 1:1:1, wherein the one or more transition metals each are coordinated with two oxygen atoms of a single one of the betaine molecules or with two oxygen atoms of two different ones of the one or more betaine molecules, wherein the transition metal is copper and the complex is characterized by an x-ray diffractogram having, for Cu-Kα1 radiation at room temperature, powder x-ray diffraction peaks at 10.8, 12.3, 14.8, 17.4, 19.6, 19.9, 21.2, and 25.2 in degrees 2-theta, each with a standard deviation of +/−0.2 degrees 2-theta.

6. A complex containing one or more betaine molecules, one or more transition metals, and one or more sulfate molecules in a ratio of 1:1:1, wherein the one or more transition metals each are coordinated with two oxygen atoms of a single one of the betaine molecules or with two oxygen atoms of two different ones of the one or more betaine molecules, wherein the transition metal is manganese and the complex is characterized by an x-ray diffractogram having, for Cu-Kα1 radiation at room temperature, powder x-ray diffraction peaks at 9.7, 14.1, 18.2, 18.5, 20.5, 21.0, 24.5, and 26.9 in degrees 2-theta, each with a standard deviation of +/−0.2 degrees 2-theta.

7. A method of using the complex as claimed in claim 1 in nutrition, the method comprising providing the complex as a dietary supplement for humans or adding the complex to feed for animals.

8. A method of using the complex as claimed in claim 2 in nutrition, the method comprising providing the complex as a dietary supplement for humans or adding the complex to feed for animals.

9. A method of using the complex as claimed in claim 3 in nutrition, the method comprising providing the complex as a dietary supplement for humans or adding the complex to feed for animals.

10. A method of using the complex as claimed in claim 4 in nutrition, the method comprising providing the complex as a dietary supplement for humans or adding the complex to feed for animals.

11. A method of using the complex as claimed in claim 5 in nutrition, the method comprising providing the complex as a dietary supplement for humans or adding the complex to feed for animals.

12. A method of using the complex as claimed in claim 6 in nutrition, the method comprising providing the complex as a dietary supplement for humans or adding the complex to feed for animals.

* * * * *